United States Patent
Mansker et al.

(10) Patent No.: US 10,489,551 B2
(45) Date of Patent: Nov. 26, 2019

(54) SYSTEM AND METHOD FOR MULTI-MODALITY WORKFLOW MANAGEMENT USING HIERARCHICAL STATE MACHINES

(71) Applicant: Volcano Corporation, San Diego, CA (US)

(72) Inventors: Richard E. Mansker, Sacramento, CA (US); Bill Clark, Davis, CA (US); Rex Kerr, Folsom, CA (US); Jason Spencer, Rocklin, CA (US)

(73) Assignee: VOLCANO CORPORATION, San Diego, CA (US)

( * ) Notice: Subject to any disclaimer, the term of this patent is extended or adjusted under 35 U.S.C. 154(b) by 214 days.

(21) Appl. No.: 14/103,570

(22) Filed: Dec. 11, 2013

(65) Prior Publication Data

US 2014/0180703 A1 Jun. 26, 2014

Related U.S. Application Data

(60) Provisional application No. 61/740,024, filed on Dec. 20, 2012, provisional application No. 61/784,604, filed on Mar. 14, 2013.

(51) Int. Cl.
*G06F 19/00* (2018.01)
*G16H 30/40* (2018.01)
(Continued)

(52) U.S. Cl.
CPC .......... *G06F 19/321* (2013.01); *G16H 30/00* (2018.01); *G16H 30/20* (2018.01); *G16H 30/40* (2018.01)

(58) Field of Classification Search
CPC .................................................. A61B 5/0035
See application file for complete search history.

(56) References Cited

U.S. PATENT DOCUMENTS 6,353,445 B1 3/2002 Babula et al.
7,224,185 B2 * 5/2007 Campbell et al. .............. 326/46
(Continued)

FOREIGN PATENT DOCUMENTS

WO WO 2012/138872 10/2012

OTHER PUBLICATIONS

Harel, David, Statecharts: A Visual Formalism for Complex Systems, 1987, Science of Computer Programming, vol. 8, pp. 231-274.*

(Continued)

*Primary Examiner* — Devin C Hein

(57) ABSTRACT

A multi-modality medical system having a computing system communicatively coupled to a medical instrument is provided. An acquisition control activity module is configured to control acquisition of medical data from a patient with the medical instrument and a business logic state machine having a first data acquisition state and a first data review state and being operable to utilize the acquisition control activity module to control acquisition of medical data from the patient with the medical instrument while in the first data acquisition state, and being configured to convert the medical data into images representative of portions of the patient while in the first data acquisition state. The computing system includes also includes a user interface state machine having a second data acquisition state and a second data review state and being configured to present the images within a user interface while in the second data review state.

28 Claims, 8 Drawing Sheets

(51) Int. Cl.
*G16H 30/00* (2018.01)
*G16H 30/20* (2018.01)

(56) References Cited

U.S. PATENT DOCUMENTS

| | | | |
|---|---|---|---|
| 2003/0069651 A1* | 4/2003 | Mathew | G05B 19/042 |
| | | | 700/31 |
| 2004/0218599 A1* | 11/2004 | Kobayashi | G06F 3/14 |
| | | | 370/389 |
| 2006/0152516 A1* | 7/2006 | Plummer | G06F 19/321 |
| | | | 345/538 |
| 2006/0264749 A1 | 11/2006 | Weiner et al. | |
| 2007/0214017 A1 | 9/2007 | Profio et al. | |
| 2009/0150184 A1 | 6/2009 | Spahn | |
| 2010/0295870 A1 | 11/2010 | Baghdadi et al. | |
| 2011/0145274 A1 | 6/2011 | Avinash et al. | |
| 2012/0310081 A1* | 12/2012 | Adler et al. | 600/427 |

OTHER PUBLICATIONS

Almeida, E., Luntz, J., & Tilbury, D. M. (Jul. 2005). Modular finite state machines implemented as event-condition-action systems. In Proceedings of the Ifac world congress. Prague. Google Scholar (Year: 2005).*

International Searching Authority/Korean Intellectual Property Office, "Notification of Transmittal of the International Search Report and the Written Opinion of the International Searching Authority, or the Declaration," for PCT/US2013/074264, dated Sep. 25, 2014, 11 pages.

International Searching Authority/European Patent Office, "Communication—Supplementary European Search Report," for European Application No. 13864210.3, dated Jul. 28, 2016, 6 pages.

* cited by examiner

SYSTEM AND METHOD FOR MULTI-MODALITY WORKFLOW MANAGEMENT USING HIERARCHICAL STATE MACHINES

CROSS-REFERENCE TO RELATED APPLICATIONS

The present application claims priority to and the benefit of U.S. Provisional Patent Application No. 61/740,024, filed Dec. 20, 2012, and U.S. Provisional Patent Application No. 61/784,604, filed Mar. 14, 2013, each of which is hereby incorporated by reference in its entirety.

TECHNICAL FIELD

Embodiments of the present disclosure relate generally to the field of medical devices and, more particularly, to systems and methods for multi-modality workflow management using hierarchical state machines.

BACKGROUND

Innovations in diagnosing and verifying the level of success of treatment of disease have migrated from external imaging processes to internal diagnostic processes. In particular, diagnostic equipment and processes have been developed for diagnosing vasculature blockages and other vasculature disease by means of ultra-miniature sensors placed upon the distal end of a flexible elongate member such as a catheter, or a guide wire used for catheterization procedures. For example, known medical sensing techniques include angiography, intravascular ultrasound (IVUS), forward looking IVUS (FL-IVUS), fractional flow reserve (FFR) determination, a coronary flow reserve (CFR) determination, optical coherence tomography (OCT), transesophageal echocardiography, and image-guided therapy. Each of these techniques may be better suited for different diagnostic situations. To increase the chance of successful treatment, health care facilities may have a multitude of imaging, treatment, diagnostic, and sensing modalities on hand in a catheter lab during a procedure. However, each imaging modality in a catheter lab traditionally requires its own special-purpose diagnostic equipment. For instance, an imaging modality may require a catheter, a patient isolation module (PIM), a user control interface, a display, a specialized power unit, and a processing unit such as a customized personal computer. Traditionally, all of this equipment is located in the catheter room itself during a procedure and depends on a substantial wiring infrastructure for connectivity and dependable power. Physical space is typically at a premium in catheter labs and each additional imaging modality employed in a catheter lab complicates the pre-procedure setup and limits the movement of health care professionals during procedures. Additionally, each imaging modality device must be independently setup and managed by a clinician trained to operate the unique controls of the specific devices. This may not be convenient, given the limits of patient safety, procedure time, staffing and the availability of sufficiently trained personnel. Further, current integrated software solutions that combine multiple imaging modalities are difficult to upgrade and are otherwise problematic.

Accordingly, while the existing medical data acquisition and treatment systems and methods have been generally adequate for their intended purposes, they have not been entirely satisfactory in all respects.

SUMMARY

Generally, the present disclosure is directed to managing acquisition and treatment workflows in multi-modality medical processing system using hierarchical state machines. A multi-modality medical system acquires, stores, processes, and displays data associated with a plurality of different medical modalities. Independent modules within the medical system handle modality workflows through the use of state machines. Each state machine in a modality workflow component may implement a different aspect of the acquisition workflow. For example, one state machine may be configured to control data acquisition and one state machine may be configured to control a user interface. Such compartmentalization of component functionality simplifies workflow implementation and therefore reduces the chance of malfunction or error during an acquisition or therapy procedure being performed on a patient.

In one exemplary aspect, the present disclosure is directed a multi-modality medical system that includes a computing system communicatively coupled to a first medical instrument and a second medical instrument. The computing system includes a first business logic state machine configured to control acquisition of first medical data from a patient with the first medical instrument, the first medical data being in a first medical modality and a second business logic state machine configured to control acquisition of second medical data from the patient with the second medical instrument, the second medical data being in a second medical modality different than the first medical modality. The computing system also includes a data repository configured to store the first and second medical data, a first user interface state machine configured to present the first medical data within a user interface, and a second user interface state machine configured to present the second medical data within the user interface.

In another exemplary aspect, the present disclosure is directed to a multi-modality medical system. The system includes a computing system communicatively coupled to a medical instrument. The computing system includes an acquisition control activity module configured to control acquisition of medical data from a patient with the medical instrument and a business logic state machine having a first data acquisition state and a first data review state and being operable to utilize the acquisition control activity module to control acquisition of medical data from the patient with the medical instrument while in the first data acquisition state, and being configured to convert the medical data into images representative of portions of the patient while in the first data acquisition state. The computing system includes also includes a user interface state machine having a second data acquisition state and a second data review state and being configured to present the images within a user interface while in the second data review state.

In yet another exemplary aspect, the present disclosure is directed to a multi-modality medical workflow management method performed with a computing system communicatively coupled to first and second medical instruments. The method includes acquiring, with a first business logic state machine, first medical data from a patient with the first medical instrument, the first medical data being in a first medical modality and acquiring, with a second business logic state machine, second medical data from the patient with the second medical instrument, the second medical data being in a second medical modality different than the first medical modality. The method also includes presenting, with a first user interface state machine, the first medical data within a user interface and presenting, with a second user interface state machine, the second medical data within the user interface.

DETAILED DESCRIPTION

Figure 1:
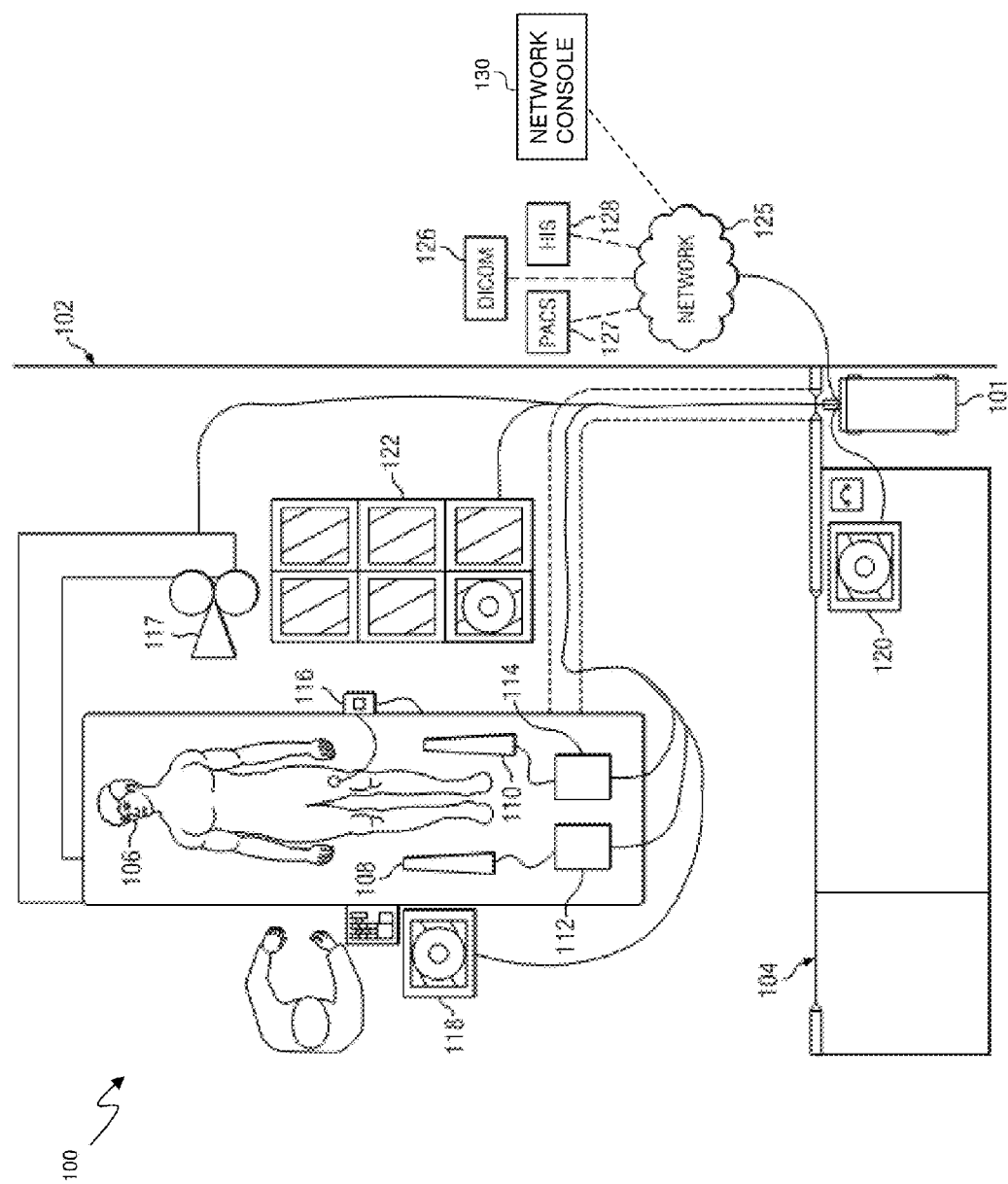
FIG. 1 is a schematic drawing depicting a medical system including a multi-modality processing system according to one embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic drawing depicting a medical system 100 including a multi-modality processing system 101 according to one embodiment of the present disclosure. In general, the medical system 100 provides for coherent integration and consolidation of multiple forms of acquisition and processing elements designed to be sensitive to a variety of methods used to acquire and interpret human biological physiology and morphological information and coordinate treatment of various conditions. More specifically, in system 100, the multi-modality processing system 101 is an integrated device for the acquisition, control, interpretation, and display of multi-modality medical sensing data. In one embodiment, the processing system 101 is a computer system with the hardware and software to acquire, process, and display multi-modality medical data, but, in other embodiments, the processing system 101 may be any other type of computing system operable to process medical data. In the embodiments in which processing system 101 is a computer workstation, the system includes at least a processor such as a microcontroller or a dedicated central processing unit (CPU), a non-transitory computer-readable storage medium such as a hard drive, random access memory (RAM), and/or compact disk read only memory (CD-ROM), a video controller such as a graphics processing unit (GPU), and a network communication device such as an Ethernet controller or wireless communication controller. In that regard, in some particular instances the processing system 101 is programmed to execute steps associated with the data acquisition and analysis described herein. Accordingly, it is understood that any steps related to data acquisition, data processing, instrument control, and/or other processing or control aspects of the present disclosure may be implemented by the processing system using corresponding instructions stored on or in a non-transitory computer readable medium accessible by the processing system. In some instances, the processing system 101 is portable (e.g., handheld, on a rolling cart, etc.). Further, it is understood that in some instances processing system 101 comprises a plurality of computing devices. In that regard, it is particularly understood that the different processing and/or control aspects of the present disclosure may be implemented separately or within predefined groupings using a plurality of computing devices. Any divisions and/or combinations of the processing and/or control aspects described below across multiple computing devices are within the scope of the present disclosure.

In the illustrated embodiment, the medical system 100 is deployed in a catheter lab 102 having a control room 104, with the processing system 101 being located in the control room. In other embodiments, the processing system 101 may be located elsewhere, such as in the catheter lab 102, in a centralized area in a medical facility, or at an off-site location (i.e., in the cloud). The catheter lab 102 includes a sterile field generally encompassing a procedure area but its associated control room 104 may or may not be sterile depending on the requirements of a procedure and/or health care facility. The catheter lab and control room may be used to perform on a patient any number of medical sensing procedures such as angiography, intravascular ultrasound (IVUS), virtual histology (VH), forward looking IVUS (FL-IVUS), intravascular photoacoustic (IVPA) imaging, a fractional flow reserve (FFR) determination, an instantaneous wave-free ratio (iFR) determination, an x-ray angiography (XA) imaging, a coronary flow reserve (CFR) determination, optical coherence tomography (OCT), computed tomography, intracardiac echocardiography (ICE), forward-looking ICE (FLICE), intravascular palpography, transesophageal ultrasound, or any other medical sensing modalities known in the art. Further, the catheter lab and control room may be used to perform one or more treatment or therapy procedures on a patient such as radiofrequency ablation (RFA), cryotherapy, atherectomy or any other medical treatment procedure known in the art. For example, in catheter lab 102 a patient 106 may be undergoing a multi-modality procedure either as a single procedure or in combination with one or more sensing procedures. In any case, the catheter lab 102 includes a plurality of medical instruments including medical sensing devices that may collect medical sensing data in various different medical sensing modalities from the patient 106.

In the illustrated embodiment of FIG. 1, instruments 108 and 110 are medical sensing devices that may be utilized by a clinician to acquire medical sensing data about the patient 106. In a particular instance, the device 108 collects medical sensing data in one modality and the device 110 collects medical sensing data in a different modality. For instance, the instruments may each collect one of pressure, flow (velocity), images (including images obtained using ultrasound (e.g., IVUS), OCT, thermal, and/or other imaging techniques), temperature, and/or combinations thereof. The devices 108 and 110 may be any form of device, instrument, or probe sized and shaped to be positioned within a vessel, attached to an exterior of the patient, or scanned across a patient at a distance.

In the illustrated embodiment of FIG. 1, instrument 108 is an IVUS catheter 108 that may include one or more sensors such as a phased-array transducer to collect IVUS sensing data. In some embodiments, the IVUS catheter 108 may be capable of multi-modality sensing such as IVUS and IVPA sensing. Further, in the illustrated embodiment, the instrument 110 is an OCT catheter 110 that may include one or more optical sensors configured to collect OCT sensing data. In some instances, an IVUS patient interface module (PIM) 112 and an OCT PIM 114 respectively couple the IVUS catheter 108 and OCT catheter 110 to the medical system 100. In particular, the IVUS PIM 112 and the OCT PIM 114 are operable to respectively receive medical sensing data collected from the patient 106 by the IVUS catheter 108 and OCT catheter 110 and are operable to transmit the received data to the processing system 101 in the control room 104. In one embodiment, the PIMs 112 and 114 include analog to digital (A/D) converters and transmit digital data to the processing system 101, however, in other embodiments, the PIMs transmit analog data to the processing system. In one embodiment, the IVUS PIM 112 and OCT PIM 114 transmit the medical sensing data over a Peripheral Component Interconnect Express (PCIe) data bus connection, but, in other embodiments, they may transmit data over a USB connection, a Thunderbolt connection, a FireWire connection, or some other high-speed data bus connection. In other instances, the PIMs may be connected to the processing system 101 via wireless connections using IEEE 802.11 Wi-Fi standards, Ultra Wide-Band (UWB) standards, wireless FireWire, wireless USB, or another high-speed wireless networking standard.

Additionally, in the medical system 100, an electrocardiogram (ECG) device 116 is operable to transmit electrocardiogram signals or other hemodynamic data from patient 106 to the processing system 101. In some embodiments, the processing system 101 may be operable to synchronize data collected with the catheters 108 and 110 using ECG signals from the ECG 116. Further, an angiogram system 117 is operable to collect x-ray, computed tomography (CT), or magnetic resonance images (MRI) of the patient 106 and transmit them to the processing system 101. In one embodiment, the angiogram system 117 may be communicatively coupled to the processing system to the processing system 101 through an adapter device. Such an adaptor device may transform data from a proprietary third-party format into a format usable by the processing system 101. In some embodiments, the processing system 101 may be operable to co-register image data from angiogram system 117 (e.g., x-ray data, MRI data, CT data, etc.) with sensing data from the IVUS and OCT catheters 108 and 110. As one aspect of this, the co-registration may be performed to generate three-dimensional images with the sensing data.

A bedside controller 118 is also communicatively coupled to the processing system 101 and provides user control of the particular medical modality (or modalities) being used to diagnose the patient 106. In the current embodiment, the bedside controller 118 is a touch screen controller that provides user controls and diagnostic images on a single surface. In alternative embodiments, however, the bedside controller 118 may include both a non-interactive display and separate controls such as physical buttons and/or a joystick. In the integrated medical system 100, the bedside controller 118 is operable to present workflow control options and patient image data in graphical user interfaces (GUIs). As will be described in greater detail in association with FIG. 2, the bedside controller 118 includes a user interface (UI) framework service through which workflows associated with multiple modalities may execute. Thus, the bedside controller 118 is capable displaying workflows and diagnostic images for multiple modalities allowing a clinician to control the acquisition of multi-modality medical sensing data with a single interface device.

A main controller 120 in the control room 104 is also communicatively coupled to the processing system 101 and, as shown in FIG. 1, is adjacent to catheter lab 102. In the current embodiment, the main controller 120 is similar to the bedside controller 118 in that it includes a touch screen and is operable to display multitude of GUI-based workflows corresponding to different medical sensing modalities via a UI framework service executing thereon. In some embodiments, the main controller 120 may be used to simultaneously carry out a different aspect of a procedure's workflow than the bedside controller 118. In alternative embodiments, the main controller 120 may include a non-interactive display and standalone controls such as a mouse and keyboard.

The medical system 100 further includes a boom display 122 communicatively coupled to the processing system 101. The boom display 122 may include an array of monitors, each capable of displaying different information associated with a medical sensing procedure. For example, during an IVUS procedure, one monitor in the boom display 122 may display a tomographic view and one monitor may display a sagittal view.

Further, the multi-modality processing system 101 is communicatively coupled to a data network 125. In the illustrated embodiment, the data network 125 is a TCP/IP-based local area network (LAN), however, in other embodiments, it may utilize a different protocol such as Synchronous Optical Networking (SONET), or may be a wide area network (WAN). The processing system 101 may connect to various resources via the network 125. For example, the processing system 101 may communicate with a Digital Imaging and Communications in Medicine (DICOM) system 126, a Picture Archiving and Communication System (PACS) 127, and a Hospital Information System (HIS) 128 through the network 125. Additionally, in some embodiments, a network console 130 may communicate with the multi-modality processing system 101 via the network 125 to allow a doctor or other health professional to access the aspects of the medical system 100 remotely. For instance, a user of the network console 130 may access patient medical data such as diagnostic images collected by multi-modality processing system 101, or, in some embodiments, may monitor or control one or more on-going procedures in the catheter lab 102 in real-time. The network console 130 may be any sort of computing device with a network connection such as a PC, laptop, smartphone, tablet computer, or other such device located inside or outside of a health care facility.

Additionally, in the illustrated embodiment, medical sensing tools in system 100 discussed above are shown as communicatively coupled to the processing system 101 via a wired connection such as a standard copper link or a fiber optic link, but, in alternative embodiments, the tools may be connected to the processing system 101 via wireless connections using IEEE 802.11 Wi-Fi standards, Ultra Wide-Band (UWB) standards, wireless FireWire, wireless USB, or another high-speed wireless networking standard.

One of ordinary skill in the art would recognize that the medical system 100 described above is simply an example embodiment of a system that is operable to collect diagnostic data associated with a plurality of medical modalities. In alternative embodiments, different and/or additional tools may be communicatively coupled to the processing system 101 so as to contribute additional and/or different functionality to the medical system 100.

Figure 2:
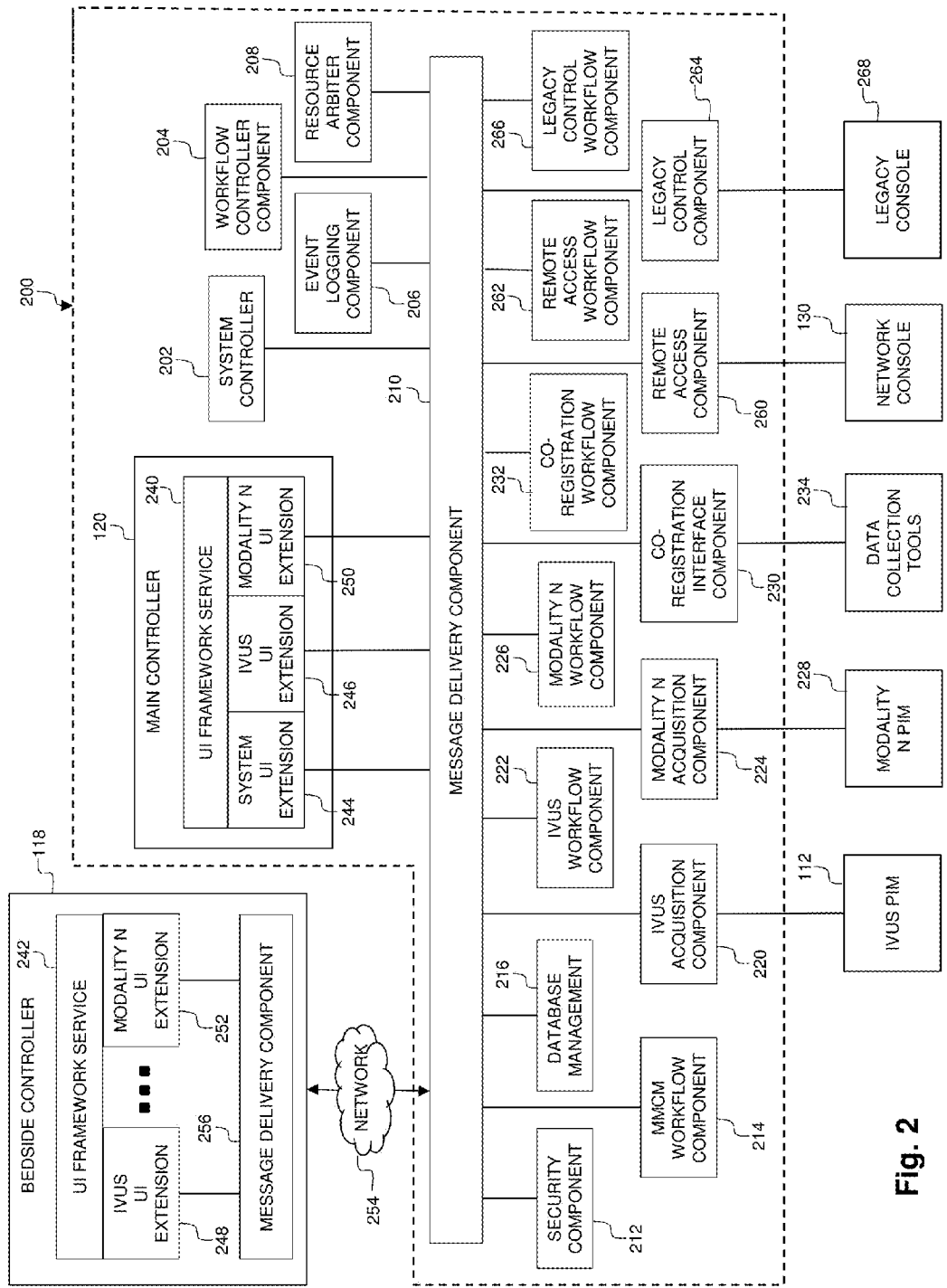
FIG. 2 is a functional block diagram of portions of the medical system, including a processing framework executing on an embodiment of the multi-modality processing system.

With reference now to FIG. 2, illustrated is a functional block diagram of portions of the medical system 100, including a processing framework 200 executing on an embodiment of the multi-modality processing system 101. The processing framework 200 includes various independent and dependent executable components that control the operation of the processing system 101, including the acquisition, processing, and display of multi-modality medical sensing data. In general, the processing framework 200 of processing system 101 is modular and extensible. That is, the framework 200 is comprised of independent software and/or hardware components (or extensions) respectively associated with different functions and medical sensing modalities. This modular design allows the framework to be extended to accommodate additional medical sensing modalities and functionality without impacting existing functionality or requiring changes to the underlying architecture. Further, an internal messaging system facilitates independent data communication between modules within the framework. In one instance, the processing framework 200 may be implemented as computer-executable instructions stored on a non-transitory computer-readable storage medium in the processing system 10. In other instances the processing framework 200 may be a combination of hardware and software modules executing within with the processing system 101.

Generally, in the embodiment shown in FIG. 2, processing framework 200 includes a plurality of components that are configured to receive medical sensing data from a plurality of medical sensing devices, process the data, and output the data as diagnostic images via the main controller 120, the bedside controller 118, or other graphical display device. The framework 200 includes several system-level components that manage the core system functions of the processing system 101 and also coordinate the plurality of modality-specific components. For instance, the framework 200 includes a system controller 202 that coordinates startup and shutdown of the plurality of executable components of the processing framework 200, including hardware and software modules related to acquisition and processing of patient diagnostic data. The system controller 202 is also configured to monitor the state of components executing within the framework 202, for instance, to determine if any components have unexpectedly stopped executing. In addition, the system controller 202 provides an interface through which other framework components may obtain system configuration and status information. Because the software framework 200 is modular, the system controller 202 is independent of the components within the framework that it manages so that errors and changes made to components do not affect the execution or structure of the system controller.

As mentioned above, the framework 200 is configured such that various extensions may be added and removed without system architecture changes. In certain embodiments, an extension executing within framework 200 may include a plurality of executable components that together implement the full functionality of the extension. In such embodiments, an extension may include an extension controller that is similar to the system controller 202 that is operable to startup, shutdown, and monitor the various executable components associated with the extension. For example, upon system startup, the system controller 202 may start an extension controller corresponding to a medical modality, and then the extension controller may, in turn, start the executable components associated with the modality. In one embodiment, extension controllers may be unallocated until system controller 202 associates them with a specific modality or other system task via parameters retrieved from a configuration mechanism, such as a configuration file.

The processing framework 200 further includes a workflow controller component 204 that is generally configured to govern the execution of the executable components of the framework 202 during multi-modality medical sensing workflows. The workflow controller component 204 may govern workflows executed by the processing framework 200 in various different manners.

The processing framework 200 further includes an event logging component 206 that is configured to log messages received from various components of the processing framework. For instance, during system startup, the system controller 202 may send messages about the status of components being started to the event logging component 206 which, in turn, writes the messages to a log file in a standardized format. Additionally, the processing framework 200 includes a resource arbiter component 208 that is configured to manage the sharing of limited system resources between various executable components of the framework 202 during multi-modality medical sensing and/or treatment workflows. For example, during a multi-modality workflow, two or more components associated with different modalities within the processing framework 202 may be vying for the same system resource such as a graphical display on the main controller 120. The resource arbiter component 208 may coordinate sharing of limited system resources in various manners such as through a lock system, a queue system, or a hierarchical collision management system.

In one embodiment, the system controller 202, workflow controller component 204, event logging component 206, and resource arbiter component 208 may be implemented as processor-executable software stored on non-transitory, computer-readable storage medium, but in alternative embodiments, these components may be implemented as hardware components such as special purpose microprocessors, Field Programmable Gate Arrays (FPGAs), microcontrollers, graphics processing units (GPU), digital signal processors (DSP). Alternatively, the components of the processing framework may be implemented as a combination of hardware and software. In certain embodiments in which executable components are implemented in FPGAs, the system controller 202 may be configured to dynamically alter the programmable logic within the FPGAs to implement various functionality needed at the time. As an aspect of this, the processing system 101 may include one or more unassigned FPGAs that may be allocated by the system controller during system startup. For instance, if upon startup of the processing system 101, the system controller detects an OCT PIM and catheter coupled thereto, the system controller or an extension controller associated with OCT functionality may dynamically transform the programmable logic within one the unassigned FPGAs such that it includes functionality to receive and/or process OCT medical data.

To facilitate intersystem communication between different hardware and software components in the multi-modality processing system 101, the processing framework 200 further includes a message delivery component 210. In one embodiment, the message delivery component 210 is configured to receive messages from components within the framework 202, determine the intended target of the messages, and deliver the messages in timely manner (i.e., the message delivery component is an active participant in the delivery of messages). In such an embodiment, message metadata may be generated by the sending component that includes destination information, payload data (e.g., modality type, patient data, etc.), priority information, timing information, or other such information. In another embodiment, message delivery component 210 may be configured to receive messages from components within the framework 202, temporarily store the messages, and make the messages available for retrieval by other components within the framework (i.e., the message delivery component is a passive queue). In any case, the message delivery component 210 facilitates communication between executable components in the framework 200. For instance, the system controller 202 may utilize the message delivery component 210 to inquire into the status of components starting up during a system startup sequence, and then, upon the receiving status information, utilize the message delivery component to transmit the status information to the event logging component 206 so that it may be written to a log file. Similarly, the resource arbiter component 208 may utilize the message delivery component 210 to pass a resource token between components requesting access to limited resources.

In one example embodiment in which the message delivery component 210 is a passive queue, components in the framework 200 may packetize incoming medical sensing data into messages and then transmit the messages to a queue on the message delivery component where they may be retrieved by other components such as image data processing components. Further, in some embodiments, the message delivery component 210 is operable to make received messages available in a First-In-First-Out (FIFO) manner, wherein messages that arrive on the queue first will be removed from the queue first. In alternative embodiments, the message delivery component 210 may make messages available in a different manner for instance by a priority value stored in a message header. In one embodiment, the message delivery component 210 is implemented in random-access memory (RAM) in the processing system 101, but, in other embodiments, it may be implemented in non-volatile RAM (NVRAM), secondary storage (e.g., magnetic hard drives, flash memory, etc.), or network-based storage. Further, in one embodiment, messages stored on the message delivery component 210 may be accessed by software and hardware modules in processing system 101 using Direct Memory Access (DMA).

The processing framework 202 further includes a number of additional system components that provide core system functionality including a security component 212, a multi-modality case management (MMCM) component 214, and a database management component 216. In certain embodiments, the security component 212 is configured to provide various security services to the overall processing framework and to individual components. For example, components implementing an IVUS data acquisition workflow may utilize encryption application programming interfaces (APIs) exposed by the security component 212 to encrypt IVUS data before it is transmitted over a network connection. Further, the security component 212 may provide other security services, such as system-level authentication and authorization services to restrict access to the processing framework to credentialed users and also to prevent the execution of untrusted components within the extensible framework. The multi-modality case management (MMCM) component 214 is configured to coordinate and consolidate diagnostic data associated with a plurality of medical modalities into a unified patient record that may be more easily managed. Such a unified patient record may be more efficiently stored in a database and may be more amenable to data archival and retrieval. In that regard, the database management component 216 is configured to present transparent database services to the other components in the framework 200 such that database connection and management details are hidden from the other components. For example, in certain embodiments, the database management component 216 may expose an API that includes database storage and retrieval functionality to components of the framework 200. In other words, a medical sensing workflow component may be able to transmit diagnostic data to a local and/or remote database such as a DICOM or PACS server via the database component without being aware of database connection details. In other embodiments, the database management component 216 may be operable perform additional and/or different database services such as data formatting services that prepare diagnostic data for database archival.

As mentioned above, the processing framework 200 of the multi-modality processing system 101 is operable to receive and process medical data associated with a plurality of modalities. In that regard, the processing framework 200 includes a plurality of modular acquisition components and workflow components that are respectively associated with different medical sensing and diagnostic modalities. For instance, as shown in the illustrated embodiment of FIG. 2, the processing framework 200 includes an IVUS acquisition component 220 and an IVUS workflow component 222 that are respectively configured to receive and process IVUS medical sensing data from the IVUS PIM 112. In accordance with the modular and extensible nature of the processing framework 200, any number of additional acquisition and workflow components may be independently added to the framework as denoted by the modality "N" acquisition component 224 and the modality "N" workflow component 226 that acquire and process data from a modality "N" PIM 228. For example, in certain embodiments, the processing system 101 may be communicatively coupled to the OCT PIM 114, the ECG system 116, a fractional flow reserve (FFR) PIM, a FLIVUS PIM, and an ICE PIM. In other embodiments, additional and/or different medical sensing, treatment, or diagnostic devices may be coupled to the processing system 101 via additional and/or different data communication connections known in the art. In such a scenario, in addition to the IVUS acquisition module 220, the processing framework 200 may include an FFR acquisition component to receive FFR data from an FFR PIM, a FLIVUS acquisition component to receive FLIVUS data from a FLIVUS PIM, an ICE acquisition component to receive ICE data from an ICE PIM, and an OCT acquisition component is operable to receive OCT data from an OCT PIM. In this context, medical data communicated between the executable components of the processing framework 200 and the communicatively coupled medical devices (e.g., PIMs, catheters, etc.) may include data collected by sensors, control signals, power levels, device feedback, and other medical data related to a sensing, treatment, or diagnostic procedure. Further, in certain embodiments, patient treatment devices may be communicatively coupled to the processing system 101 such as devices associated with radiofrequency ablation (RFA), cryotherapy, or atherectomy and any PIMs or other control equipment associated with such treatment procedures. In such an embodiment, the modality "N" acquisition component 224 and the modality "N" workflow component 226 may be configured to communicate with and control the treatment devices such as by relaying control signals, relaying power levels, receiving device feedback, and receiving data collected by sensors disposed on the treatment devices.

In one embodiment, once the acquisition components 220 and 224 have received data from connected medical sensing devices, the components packetize the data into messages to facilitate intersystem communication. Specifically, the components may be operable to create a plurality of messages from an incoming digital data stream, where each message contains a portion of the digitized medical sensing data and a header. The message header contains metadata associated with the medical sensing data contained within the message. Further, in some embodiments, the acquisition components 220 and 224 may be operable to manipulate the digitized medical sensing data in some way before it is transmitted to other portions of the framework 200. For example, the acquisition components may compress the sensing data to make intersystem communication more efficient, or normalize, scale or otherwise filter the data to aid later processing of the data. In some embodiments, this manipulation may be modality-specific. For example, the IVUS acquisition component 220 may identify and discard redundant IVUS data before it is passed on to save processing time in subsequent steps. The acquisition components 220 and 224 may additionally perform a number of tasks related to the acquisition of data including responding to interrupts generated by data buses (e.g., PCIe, USB), detecting which medical sensing devices are connected to processing system 101, retrieving information about connected medical sensing devices, storing sensing device-specific data, and allocating resources to the data buses. As mentioned above, the data acquisition components are independent from each other and may be installed or removed without disrupting data acquisition by other components. Additionally, acquisition components are independent of underlying data bus software layers (for example, through the use of APIs) and thus may be created by third parties to facilitate acquisition of data from third party medical sensing devices.

The workflow components of the processing framework, such as the IVUS workflow component 222, receive unprocessed medical sensing and/or diagnostic data from respective acquisition components via the message delivery component 210. In general, the workflow components are configured to control the acquisition of medical sensing data such as by starting and stopping data collection at calculated times, displaying acquired and processed patient data, and facilitating the analysis of acquired patient data by a clinician. As an aspect of this, the workflow components are operable to transform unprocessed medical data gathered from a patient into diagnostic images or other data formats that enable a clinician to evaluate a patient's condition. For example, an IVUS workflow component 222 may interpret IVUS data received from the IVUS PIM 112 and convert the data into human-readable IVUS images. In one embodiment, a software stack within the framework may expose a set of APIs with which the workflow component 222 and other workflow components in the framework may call to access system resources such as the computational resources, the message delivery component 210, and communication resources. After processing acquired data, the modality-centric workflow components may transmit one or more messages containing the processed data to other components within the framework 200 via the message delivery component 210. In some embodiments, before sending such messages, the components may insert a flag in the header indicating that the message contains processed data. Additionally, in some embodiments, after processing medical sensing data, the components may utilize the database management component 216 to transmit the processed data to archival systems such as a locally attached mass storage device or the network-based PACS server 127. In accordance with the modular architecture of the processing framework 200, the workflow components 222 and 226 are independent of each other and may be installed or removed without disrupting other components, and may be written by third parties. Further, due to their independence, they may be are operable to process signaling and imaging data from multiple medical sensing devices concurrently.

The processing framework 200 additionally includes a co-registration interface component 230 and a co-registration workflow component 232 that are configured to acquire and process data from any number of data collection tools 234 and co-register the acquired data with data acquired by one of the other acquisition components within the framework. In more detail, the co-registration interface component 230 may be operable to communicatively interface with medical data acquisition tools associated with any number of modalities, such as the ECG device 116 or the angiography system 117 of FIG. 1. In certain embodiments, the interface component 230 may be operable to standardize and/or transform incoming modality data such that it may be co-registered with other sensing data acquired by the processing system 101. As medical data is being acquired by the co-registration interface component 230, the co-registration workflow component 232 is configured to facilitate the co-registration of data from different modalities such as by spatially or temporally synchronizing data collection among medical sensing devices, aligning two or more acquired data sets based on spatial or temporal registration markers, and generating co-registered diagnostic images or other human-readable data that enable a clinician to evaluate a patient's condition. Further, in other embodiments, the co-registration workflow component 232 may be operable to spatially co-register catheter-gathered data in a two-dimensional (2-D) or three-dimensional (3-D) space using previously-generated 2-D images or 3-D models. For example, a catheter-based sensing tool may include fiducials that are tracked to generate position data during a sensing procedure, and the co-registration workflow component 232 may register this position data against previously acquired MRI data. Still further, the co-registration workflow component 232 may facilitate co-registration of multi-modality data acquired by native acquisition components within the framework 200 such as the IVUS acquisition component 220 and modality "N" acquisition component 224. Additionally, in some embodiments, a real-time clock may be integrated into the co-registration workflow component 232. U.S. Provisional Patent Application No. 61/473,591, entitled "DISTRIBUTED MEDICAL SENSING SYSTEM AND METHOD", discloses temporally synchronizing medical sensing data collection in more detail and is hereby incorporated by reference in its entirety.

As discussed above in association with FIG. 1, a clinician utilizing the processing system 101 may control workflows and view diagnostic images through the main controller 120 and the bedside controller 118. The main controller 120 and the bedside controller 118 respectively include user interface (UI) framework services 240 and 242 that support a plurality of user interface (UI) extensions (or components). In general, the UI extensions supported by the UI framework services 240 and 242 respectively correspond to medical sensing modalities and are operable to render a user interface for control of the associated acquisition workflow and display of processed sensing data. Similar to the processing framework 200, the UI frameworks 240 and 242 are extensible in that they support UI extensions that are independent of one another. That is, its modular design allows the UI frameworks 240 and 242 to be extended to accommodate additional medical sensing modality user interfaces without impacting existing user interfaces or requiring changes to the underlying UI architectures. In the illustrated embodiment, the main controller 120 includes a system UI extension 244 that renders a user interface containing core system controls and configuration options. For example, a clinician may startup, shutdown or otherwise manage the processing system 101 using the user interface rendered by the system UI extension 244. In one embodiment, the components of the main controller 120 may be considered part of the processing framework 200. The IVUS UI extensions 246 and 248 render user interfaces for the main controller 120 and bedside controller 118, respectively. For example, the IVUS UI extensions 246 and 248 may render and display the touch screen buttons used to control an IVUS workflow and also render and display the IVUS diagnostic images created by the IVUS workflow component 222. Similarly, the modality "N" UI extensions 250 and 252 render controls and images associated with a modality "N" workflow.

In one embodiment, the UI framework services 240 and 242 may expose APIs with which the UI extensions may call to access system resources such as a look-and-feel toolbox and error handling resources. Look-and-feel toolbox APIs enable the UI extensions to present a standardized user interface with common buttons, parallel workflow formats, and data presentation schemes for different modality workflows. In this manner, clinicians may more easily transition between acquisition modalities without additional user interface training. Further, co-registration UI extensions may present and/or combine processed image or signaling data from multiple modalities. For instance, a UI extension may display an electrocardiogram (ECG) wave adjacent to IVUS imaging data or may display an IVUS image overlaid with borders that were previously drawn on an OCT image. Further, in some embodiments, the UI framework services 240 and 242 may include a multi-tasking framework to coordinate concurrently executing UI extensions. For instance, in the event the processing system 101 is simultaneously acquiring data associated with more than one modality, the UI framework services 240 and 242 may present the user with a modality selector screen on which a desired user interface may be selected.

The UI framework service 240 communicates with the components of the processing framework 200 via the message delivery component 210. As shown in the illustrated embodiment of FIG. 2, the bedside controller 118 may be communicatively coupled to the processing framework 200 via a network connection 254. The network connection 254 may be any type of wired of wireless network connection such as an Ethernet connection or IEEE 802.11 Wi-Fi connection. Alternatively, one or both of the main and bedside controllers 120 and 118 may communicate with the processing framework 200 via a local bus connection such as a (PCIe) data bus connection, a USB connection, a Thunderbolt connection, a FireWire connection, or some other high-speed data bus connection. Further, in the illustrated embodiment of FIG. 2, the bedside controller includes a message delivery component 256 that is configured to facilitate message-based communication between the UI extensions in the bedside controller 118 and the components in the processing framework 200. In certain embodiments, the message delivery component 256 may extract diagnostic image data from network communication packets as they arrive over the network connection 254.

The processing framework 200 includes additional components that allow a clinician to access and/or control workflows executing in the multi-modality processing system 101. For example, the framework 200 includes a remote access component 260 that communicatively couples the network console 130 (FIG. 1) to the processing framework 200. In one embodiment, the remote access component 260 is operable to export control functionality of the processing system 101 to the network console 130, so that the network console may present workflow control functions in its user interface. In certain embodiments, the remote access component 260 may receive workflow commands from the network console 130 and forward them to a remote access workflow component 262. The remote access workflow component 262 may dictate the set of commands and diagnostic data to which a remote user may access through the network console 130. Further, the legacy control component 264 and legacy control workflow component 266 provide some level of access to modality workflow control and data to users of legacy consoles 268 (e.g. button consoles, mice, keyboards, standalone monitors).

In one embodiment, the core system components of the processing framework 200 and the additional components such as the modality-related components may be implemented as processor-executable software stored on non-transitory, computer-readable storage medium, but in alternative embodiments, these components may be implemented as hardware components such as special purpose microprocessors, Field Programmable Gate Arrays (FPGAs), microcontrollers, graphics processing units (GPU), digital signal processors (DSP). Alternatively, the components of the processing framework may be implemented as a combination of hardware and software.

One of ordinary skill in the art will recognize that the processing framework 200 of FIG. 2 is simply an example embodiment and, in alternative embodiments, the framework may include different and/or additional components configured to carry out various medical sensing workflows. For instance, the processing framework 200 may further include executable components configured for the evaluation of a stenosis of a human blood vessel or configured to facilitate control of computer-assisted surgery or remotely-controlled surgery.

Figure 3:
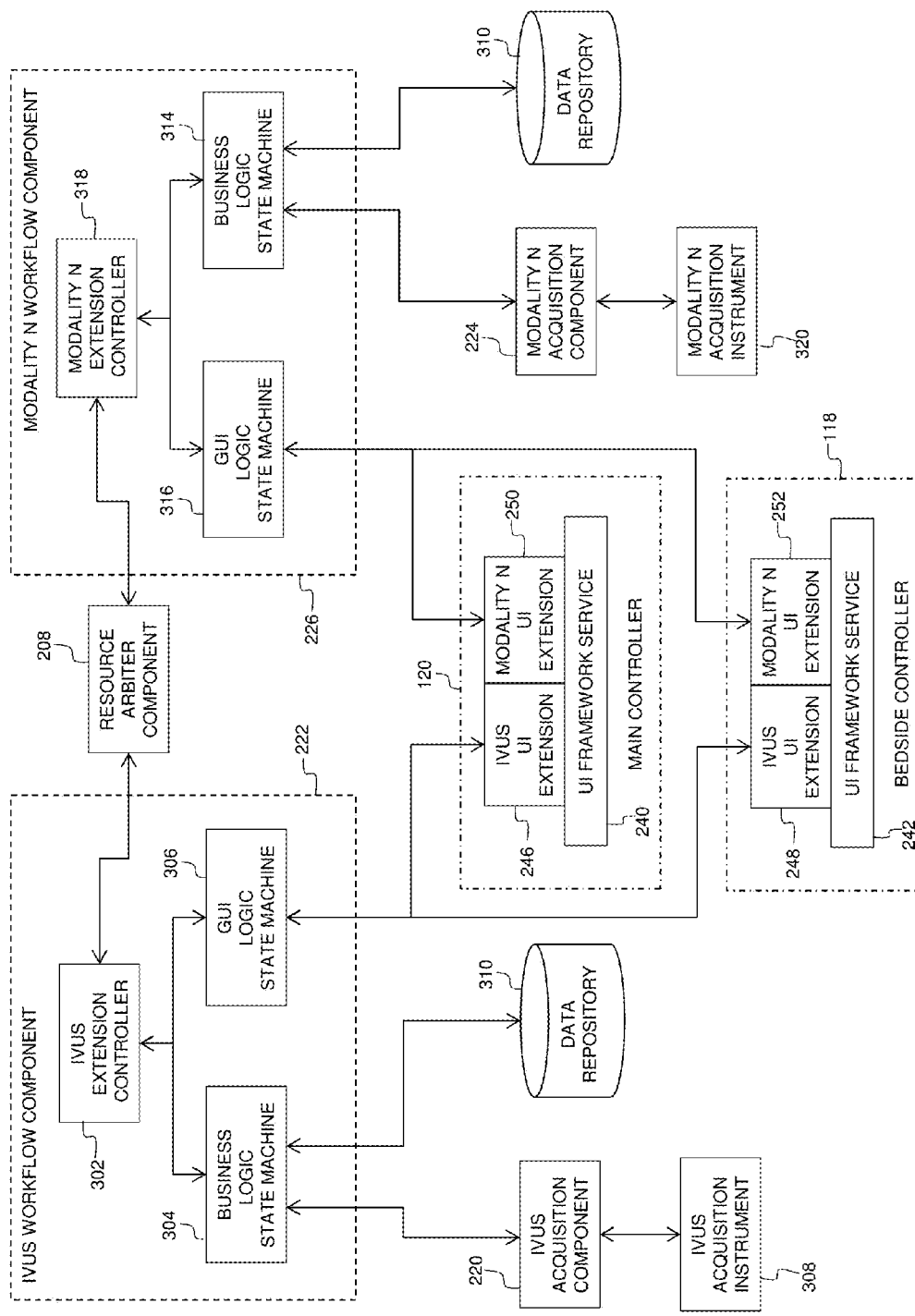
FIG. 3 is a functional block diagram of portions of the processing framework of FIG. 2, including an IVUS workflow component and a modality N workflow component.

With reference now to FIG. 3, illustrated is a functional block diagram of portions of the processing framework 200 including the IVUS workflow component 222 and the modality N workflow component 226. As described above, in the processing framework 200, each workflow component associated with a medical modality is generally configured to control a workflow to acquire medical data in that modality from a patient. In particular, each modality workflow component is configured to at least control data acquisition by a medical instrument, process raw acquired data, display processed patient data in a user interface, and facilitate the analysis of acquired medical data by a clinician. As an aspect of this, the workflow components are operable to transform unprocessed medical data gathered from a patient into diagnostic images or other data formats that enable a clinician to evaluate a patient's condition. For example, the IVUS workflow component 222 may interpret raw data received from an IVUS transducer and convert the data into human-readable IVUS images.

According to aspects of the present disclosure, the modality workflow components—such as the IVUS workflow component 222 and the modality N workflow component 226—are composed of a plurality of internal hierarchical state machines that implement the above functionality. Each state machine in a workflow component may implement a different aspect of the acquisition workflow. For example, one state machine may be configured to control data acquisition and one state machine may be configured to control a user interface. Such compartmentalization of component functionality simplifies workflow implementation and therefore reduces the chance of malfunction or error during an acquisition workflow. Patient safety is thus improved.

As shown in FIG. 3, the IVUS workflow component 222 includes an IVUS extension controller 302, a business logic state machine 304, and a graphical user interface (GUI) logic state machine 306. The extension controller 302 is configured to startup, shutdown, and monitor the various executable components associated with the IVUS workflow component 222. For example, upon system startup, the extension controller 302 may be started first and then, in turn, start and monitor the individual state machines within the workflow component 222. In that regard, methods and systems for dependency-based startup of independent components within a multi-modality medical system are disclosed in U.S. Provisional Patent Application No. 61/720,816, entitled "DEPENDENCY-BASED STARTUP IN A MULTI-MODALITY MEDICAL SYSTEM," which is hereby incorporated by reference in its entirety.

In the IVUS workflow component 222, the business logic state machine 304 is a hierarchical state machine that implements workflow functionality related to acquiring and processing IVUS data from a patient. In particular, the business logic state machine 304 has a plurality of different states corresponding to different aspects of an IVUS acquisition workflow. Each state, in turn, includes one or more activities that implement specific workflow tasks. As described in more detail in association with FIGS. 4 and 5, such activities are implemented independently so that multiple different states may reuse the same activity. Some example states and example activities of the business logic state machine 304 are also described in further detail in association with FIG. 4.

In more detail, the business logic state machine 304 is configured to control the acquisition of IVUS data from a patient. In the illustrated embodiment, the business logic state machine 304 issues commands to the IVUS acquisition component 220, which, in turn, controls an IVUS acquisition instrument 308 such an IVUS transducer that is positioned within a patient's vessel. For example, the business logic state machine 304 may transmit a command to the IVUS acquisition component 220 to begin data acquisition, and acquisition component subsequently energizes the IVUS transducer. The raw IVUS data collected by the IVUS acquisition instrument 308 is transmitted back to the business logic state machine 304 via the IVUS acquisition component 220. Upon receiving the raw IVUS data, the business logic state machine 304 is configured to convert the data into human-readable IVUS images for display to a practitioner via a user interface. In that regard, the IVUS images are transmitted to the GUI logic state machine 306 for appropriate processing. If the practitioner has elected to record the IVUS procedure, the business logic state machine 304 stores the generated IVUS images in a data repository 310. The data repository 310 may implement any type of logical data container such as a database and be stored on any type of storage medium such as a hard drive on the multi-modality processing system 101 or at a network-based storage location. In one embodiment, the repository 310 is an XML database that is accessed through a Shared Patient Information Management System (SPIMS). In some embodiments, the business logic state machine 304 stores the raw IVUS data in the data repository 310 as well. The business logic state machine 304 is further configured to retrieve stored data from the data repository 310 when a practitioner wishes to review the data or when the stored data is selected to be archived on an archival medium or remote archival database. In that regard, methods and systems for archival of multi-modality medical data are disclosed in U.S. Provisional Patent Application No. 61/746,806, entitled "MULTI-MODALITY SELECTIVE ARCHIVING SYSTEM AND METHOD," which is hereby incorporated by reference in its entirety.

The GUI logic state machine 306 is similar to the business logic state machine 304 in that it is also a hierarchical state machine with a plurality of different states corresponding to different aspects of an IVUS acquisition workflow. The states of the GUI logic state machine 306 implement workflow functionality related to displaying and reviewing acquired IVUS data in a graphical user interface. Some example states and example activities of the GUI logic state machine 306 are described in further detail in association with FIG. 5.

In more detail, the GUI logic state machine 306 is configured to render various screens and interaction elements associated with the IVUS acquisition workflow. For example, the GUI logic state machine 306 receives the IVUS images generated by the business logic state machine 304 and displays them in a display viewport. Further, when in a review state, the GUI logic state machine 306 is configured to display previously-acquired IVUS images for measurement and diagnostic purposes. The GUI logic state machine 306 operates in parallel with the business logic state machine 304 to perform multiple workflow tasks concurrently. In the illustrated embodiment, to render IVUS-specific user interface elements on the main controller 120, the GUI logic state machine 306 sends command to the IVUS UI extension 246, which, in turn, calls common rendering functions exposed by the UI framework service 240. To render IVUS-specific user interface elements on the bedside controller 118, the GUI logic state machine 306 sends commands to the IVUS UI extension 248, which, in turn, calls common rendering functions exposed by the UI framework service 242.

The IVUS workflow component 222 illustrated in the embodiment of FIG. 3 is simply an example workflow component, and, in other embodiments, the workflow component may include additional state machines that perform additional tasks related to an IVUS acquisition workflow. Further, in one embodiment, the IVUS acquisition component 220 may be implemented as a hierarchical state machine either internal or external to the IVUS workflow component 222.

In accordance with the modular and extensible nature of the processing framework 200, the multi-modality medical processing system 101 may include any number of further workflow components associated with a particular medical modality. The illustrated embodiment of FIG. 3 includes the representative modality N workflow component 226 that is similar to the IVUS workflow component 222 but is configured to implement functionality associated with a different medical modality acquisition or treatment workflow. For example, the modality N workflow component 226 may be associated with an OCT workflow, a VH workflow, a FL-IVUS workflow, an IVPA imaging workflow, a FFR workflow, an iFR workflow, an XA workflow, a CFR workflow, a computed tomography workflow, an ICE workflow, a FLICE workflow, an intravascular palpography workflow, a transesophageal ultrasound workflow, an RFA therapy workflow, a cryotherapy workflow, or an atherectomy workflow.

Like the IVUS workflow component 222, the modality N workflow component 226 includes two hierarchical state machines—a business logic state machine 314 and a GUI logic state machine 316—that are started and monitored by a modality N extension controller 318. In general, the business logic state machine 314 controls data acquisition by a modality N acquisition instrument 320 and stores modality N data in the data repository 310. The GUI logic state machine 316 is generally configured to render user interface elements and data related to a modality N acquisition or treatment workflow.

The plurality of modality workflow components in the multi-modality processing system 101 rely on common shared resources, such as the data repository 310, within the processing system, and thus some level of coordination is required to prevent resource deadlocks. In the illustrated embodiment of FIG. 3, the resource arbiter component 208 manages the utilization of shared resources by the modality components 208. In that regard, methods and systems for resource management in a multi-modality medical system are disclosed in U.S. Provisional Patent Application No. 61/739,833, entitled "RESOURCE MANAGEMENT IN A MULTI-MODALITY MEDICAL SYSTEM," which is hereby incorporated by reference in its entirety.

Figure 4:
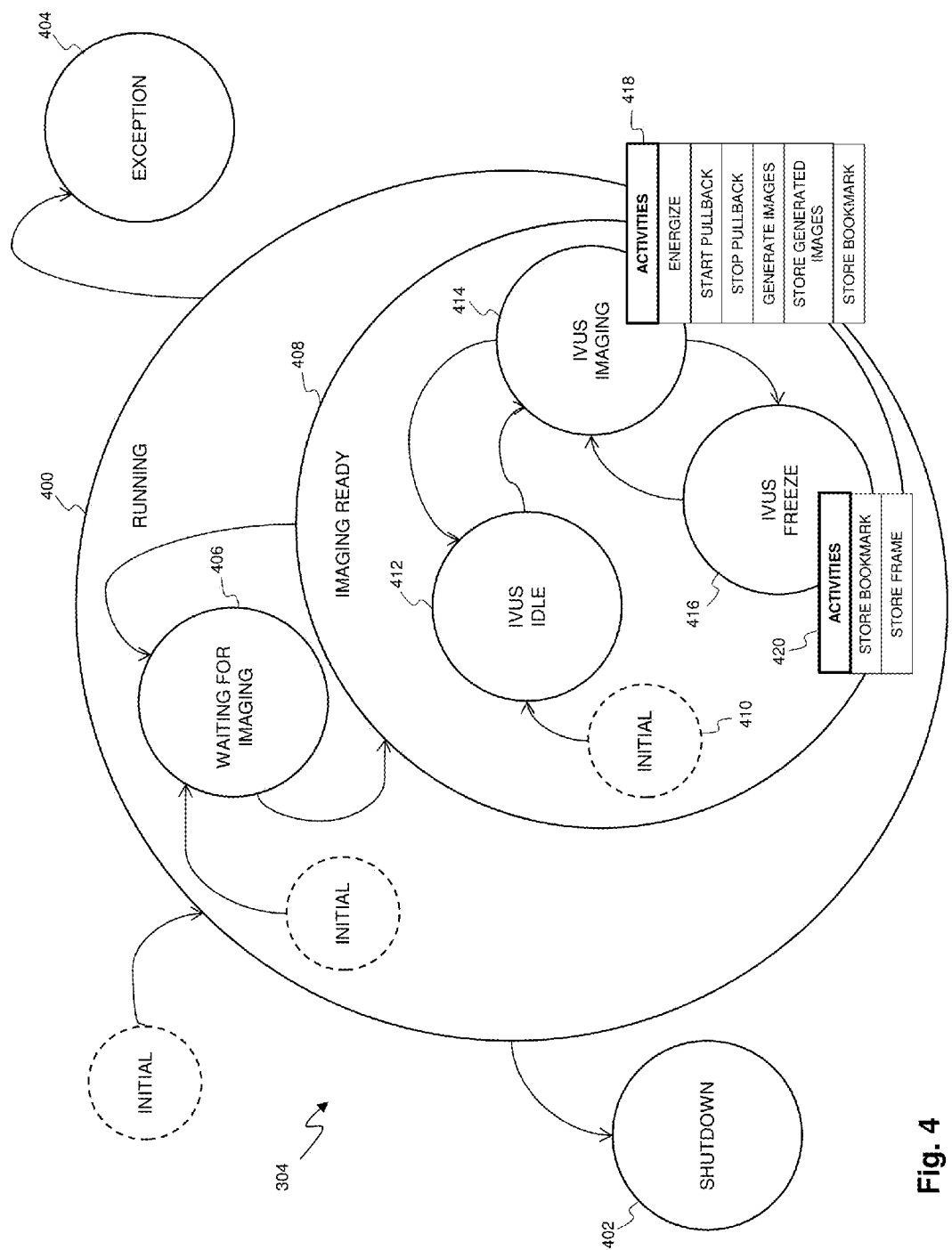
FIG. 4 illustrates a simplified state flow diagram for the business logic state machine of the IVUS workflow component shown in FIG. 3.

With reference now to FIG. 4, illustrated is a simplified state flow diagram for the business logic state machine 304 shown in FIG. 3. In particular, the state flow diagram is a hierarchical directed graph that includes a plurality of states in which the business logic state machine 304 may be during an IVUS acquisition workflow. Generally, in the context of the processing framework 200, state machines are hierarchical in that states may contain sub-state sequences nested within the enclosing state. For such nested states, there is an initial pseudo-state node which defines the transition to one of the inner states that would be followed when the enclosing state is first entered. Further, states may execute an action upon entry to the state, run an action while in the state, and execute an action upon exit from the state. During a transition between states, a transition action (or effect) can be executed. Transitions can also point back to the same state, either externally or internally. For internal transitions, a transition action is executed. For external transitions, the exit action of the source state is executed, then the transition action, then the entry action of the target state. In other words, transitions themselves are part of a state machine, but the effects that occur during transitions are resultant behavior.

Additionally, a state has three types of operations that can be defined within the state element: entry, exit, and do operations. The entry and exit operations are reserved for the entry and exit local code (i.e., code that is particular to a specific state). In contrast, the "do" operations of a state are performed with activities that may be implemented external to a state. In more detail, an activity—such as energizing a transducer—may be implemented as an independent module that may be utilized (called) by a plurality of different states in different state machines. For instance, a record state of an IVUS GUI state machine and a record state of an OCT GUI state machine may both make calls to the same activity module that renders a record button. The activity modules may be implemented as software, hardware, or some combination thereof.

In the illustrated embodiment of FIG. 4, the business logic state machine 304 includes a plurality of nested states that each may call one or more independent activities. The state machine 304 includes three top-level states: running 400, shutdown 402, and exception 404. From the running state 400, the state machine 304 transitions to the shutdown state 402 when a shutdown signal is received, and transitions to the exception state 404 when a fault is received. The running state 400 includes two sub-states: a waiting for imaging state 406 that is entered when a catheter or PIM is disconnected, and an imaging ready state 408 which, in turn, includes a number of sub-states that are entered during IVUS data capture. From an initial pseudo state 410, the state machine 304 transitions between an IVUS idle state 412, an IVUS imaging state 414, and an IVUS freeze state 416. In one instance, the state machine 304 may transition between the IVUS imaging state 414 and the IVUS freeze state 416 when a practitioner actuates a "Freeze" button on a IVUS acquisition GUI display. Notably, the states shown in FIG. 4 are simply example states and the business logic state machine 304 may have any number of additional and/or different states corresponding to various aspects of an IVUS workflow, such as an archival state.

The business logic state machine 304 transitions between the states based on triggering actions, such as a practitioner activating buttons on an GUI or on medical instruments, or connecting or disconnecting instruments such as catheters and PIMs. In that regard, whenever a state machine in a modality workflow controller transitions to a new state, it will typically begin executing some behavior (recording, archiving, displaying acquired data, etc.). To separate the details of this behavior from the transition rules, each state utilizes one or more activity modules to make this separation explicit. As mentioned above, an activity module implements the main behavior(s) associated with a state. The separation between a state and an activity provides important benefits including the reuse of the same state machine, embodying the same set of transition rules, within multiple different modality workflow components. Further, such modular activities may be reused by many different states.

In the illustrated embodiment of FIG. 4, the IVUS imaging state 414 utilizes a plurality of activities 418 that implement tasks associated with acquisition of IVUS data. For example, the activities 418 include energizing an IVUS transducer to begin collection of data within a patient's vessel, and starting and stopping pullback of a catheter on which the IVUS transducer is disposed. Further, the IVUS imaging state 414 includes an activity to convert raw IVUS data into human-readable IVUS images, and an activity to store generated IVUS images in a data repository. Further, during a real-time display of IVUS images as they are being captured, a practitioner may have the option to bookmark a specific image frame of the image stream.

As shown in FIG. 4, the IVUS freeze state 416 also includes a plurality of activities 420 that implement tasks may be performed when a live IVUS image stream is frozen, for instance by a practitioner operating a GUI. Notably, the same store bookmark activity module that is utilized by the IVUS image state 414 may also be utilized by the IVUS freeze state 416. One of ordinary skill in the art would understand that the list of activities 404 associated with the IVUS image state 414 and the IVUS freeze state 416 are simply example lists and the state 414 and 416 may include additional and/or different activities. For example, additional activities utilized by the states of the business logic state machine may include retrieving IVUS images from the data repository in response to a request initiated from a user interface. When viewing IVUS images, a practitioner may create data derived from the IVUS images, such as measurements of features represented in IVUS images, annotations of IVUS images, and labels of features in IVUS images. The data review state 402 utilizes activity modules for calculating the measurements and storing the measurements and other derived data in the data repository.

In that regard, methods and systems for enhanced measurement, manipulation, navigation, display, and annotation of multi-modality medical images are disclosed in U.S. Provisional Patent Application No. 61/746,012, entitled "DATA LABELING AND INDEXING IN A MULTI-MODALITY MEDICAL IMAGING SYSTEM," U.S. Provisional Patent Application No. 61/746,010, entitled "MEASUREMENT AND ENHANCEMENT IN A MULTI-MODALITY MEDICAL IMAGING SYSTEM," U.S. Provisional Patent Application No. 61/745,999, entitled "GESTURE-BASED INTERFACE FOR A MULTI-MODALITY MEDICAL IMAGING SYSTEM," and U.S. Provisional Patent Application No. 61/745,986, entitled "MEASUREMENT NAVIGATION IN A MULTI-MODALITY MEDICAL IMAGING SYSTEM," all of which are hereby incorporated by reference in their entirety.

Additionally, various states of a state machine in a modality workflow component different than the IVUS workflow component may utilize different activity modules. For example, a data acquisition state of a state machine in an FFR workflow component may utilize an activity module to control a sensor capturing aortic pressure, an activity to control a sensor capturing distal pressure, and an activity to perform a differential pressure calculation.

Figure 5:
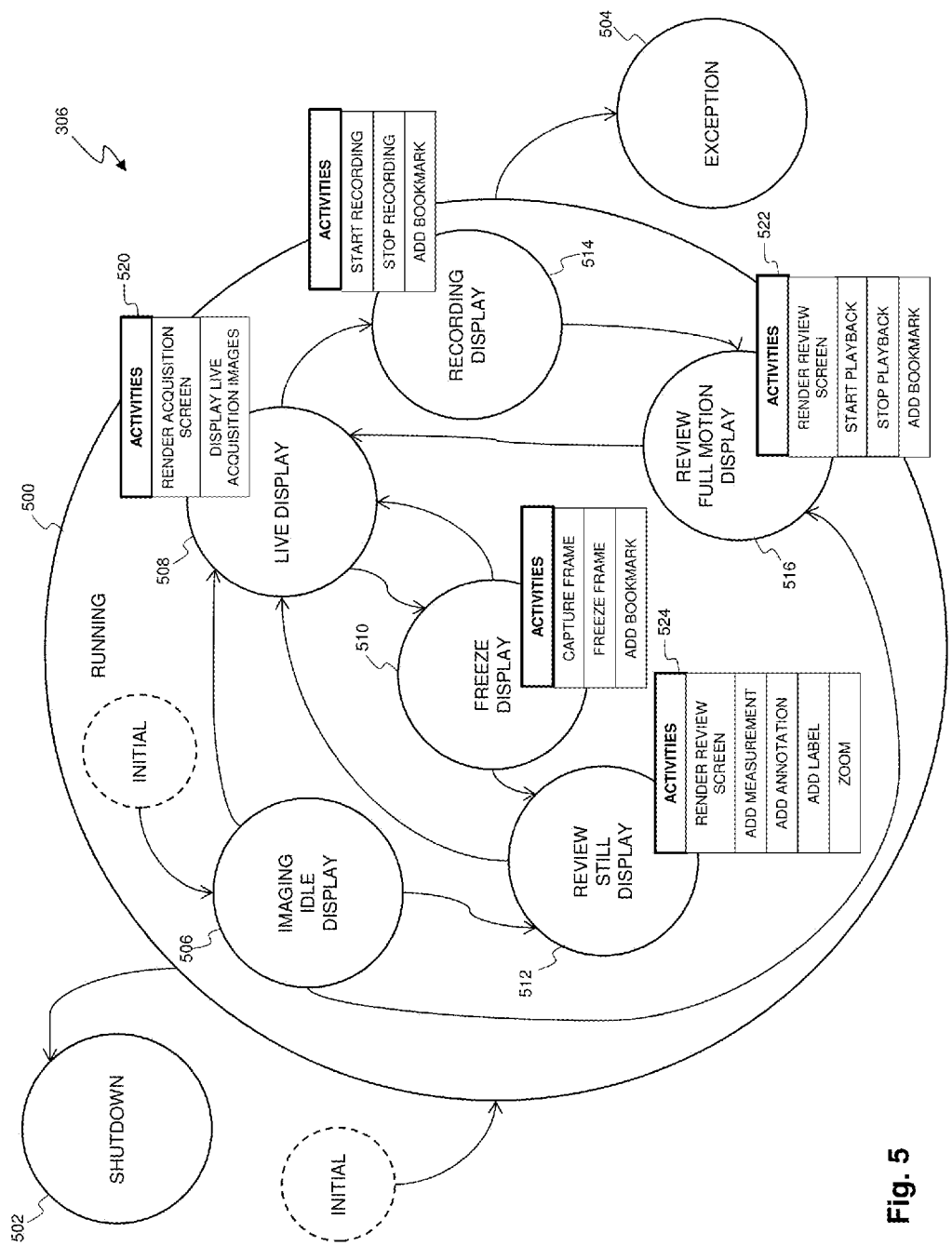
FIG. 5 illustrates is a simplified state flow diagram for the GUI logic state machine of the IVUS workflow component shown in FIG. 3.

With reference now to FIG. 5, illustrated is a simplified state flow diagram for the GUI logic state machine 306 of the IVUS workflow component 222 shown in FIG. 3. In particular, the state flow diagram shows a plurality of nested (i.e., hierarchical) states in which the GUI logic state machine 306 may be during an IVUS acquisition workflow. The states of the GUI logic state machine 306 may each call one or more independent activity modules related to rendering a user interface associated with an IVUS acquisition workflow. The state machine 306 includes three top-level states: running 500, shutdown 502, and exception 504. From the running state 500, the state machine 306 transitions to the shutdown state 502 when a shutdown signal is received, and transitions to the exception state 504 when a fault is detected. The running state 500 includes five sub-states in the illustrated embodiment: an imaging idle display state 506, a live display state 508, a freeze display state 510, a review still display state 512, a recording display state 514, and a review full motion display state 516. During an IVUS acquisition workflow, the state machine 306 transitions between the various states based on event triggers such as a practitioner actuating buttons within the GUI, actuating buttons on IVUS instruments, and connecting and disconnecting such instruments. In certain embodiments, the states of the GUI logic state machine 306 correspond to screens of the associated user interface. For example, the state machine 306 may transition between the review still display state 512 and the live display state 508 when a user switches from a data review screen to a data acquisition screen in the user interface.

The GUI logic state machine 306 is generally in one of the live display state 508, the recording display state 514, and the freeze display state 510 during acquisition of IVUS data from a patient. And, the GUI logic state machine 306 is generally in one of the review still display state 512 and the review full motion display state 516 when a practitioner is reviewing previously acquired data and generating derived data such as measurements. Notably, the states 506, 508, 510, 512, 514, and 516 are simply example states and the GUI logic state machine 306 may have any number of additional and/or different states corresponding to various aspects of an IVUS workflow. For example, the GUI logic state machine 306 may have numerous additional states that the state machine transitions between based on user actions within the user interface—e.g., a recording state may be triggered when a user actuates a record button and a measure state may be triggered when a user actuates a measure button.

Like the states of the business logic state machine 304, the states of the GUI logic state machine 306 each may utilize one or more independently-implemented activity modules that are separate from any transition condition logic used to trigger state changes. The activities of the GUI logic state machine 306 states implement user interface logic by calling the user interface functionality exposed by the IVUS UI extension 246. That is, in one embodiment, the activities do not contain the code to actually render UI elements—they contain the program logic to create the user interface layout and workflow. So, for example, when an activity needs to tell the user interface to change the screen for recording, for example by enabling and disabling the appropriate buttons, it will make the changes through an interface that any UI extension in the framework 200 implements.

Figure 6:
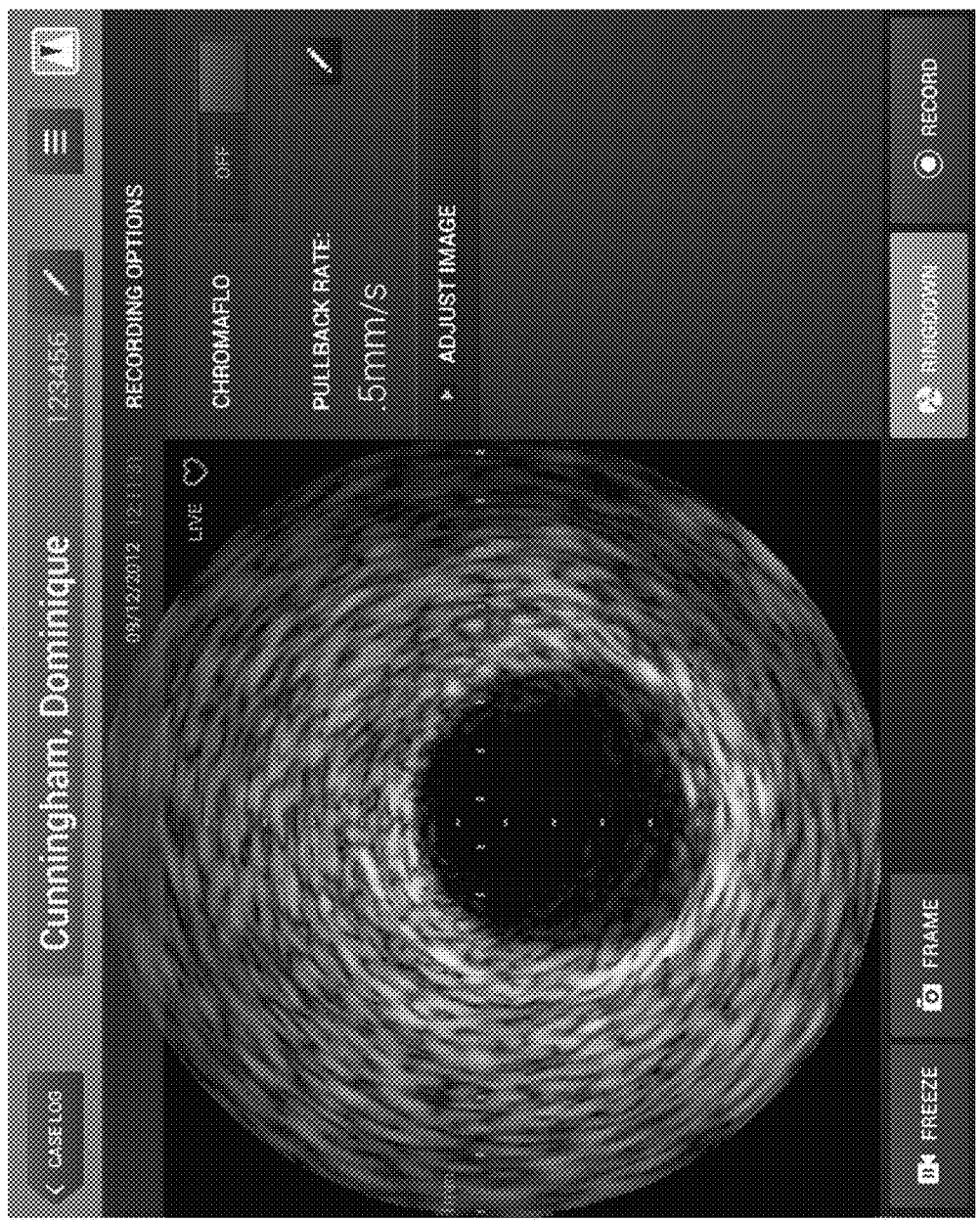
FIG. 6 illustrates an example IVUS acquisition screen of a user interface rendered by the multi-modality processing system of FIG. 1.

The live display state 508 utilizes a plurality of activities 520 that implement tasks associated with acquisition of IVUS data. For example, the activities 520 include rendering the IVUS acquisition screen including user interaction elements and displaying IVUS images as they are being captured within the acquisition screen. In that regard, an example IVUS acquisition screen is shown in detail in FIG. 6. An image of the patient's vessel as generated from data captured by an IVUS transducer is displayed to allow the practitioner to guide the delivery catheter through the patient. The activities 520 of the live display state 508 generate on-screen interaction elements such as a record button, a freeze button, and a frame capture button and capture user interaction with the on-screen elements. With reference back to FIG. 5, the recording display state 514 utilizes activity modules to handle user interface requests (such as button presses) to stop and start recording of IVUS images being captured by the IVUS transducer. Further activities include handling requests to add bookmarks to an IVUS image stream and other similar tasks. Additionally, the freeze display state 510 includes activities to capture a specific frame of an IVUS image stream, freeze an IVUS image stream, and a bookmark associated with a frozen image. One of ordinary skill in the art would understand that the lists of activities associated with the live display state 508, the recording display state 514, and the freeze display state 510 are simply example lists and the states may utilize additional and/or different activity modules.

Figure 7:
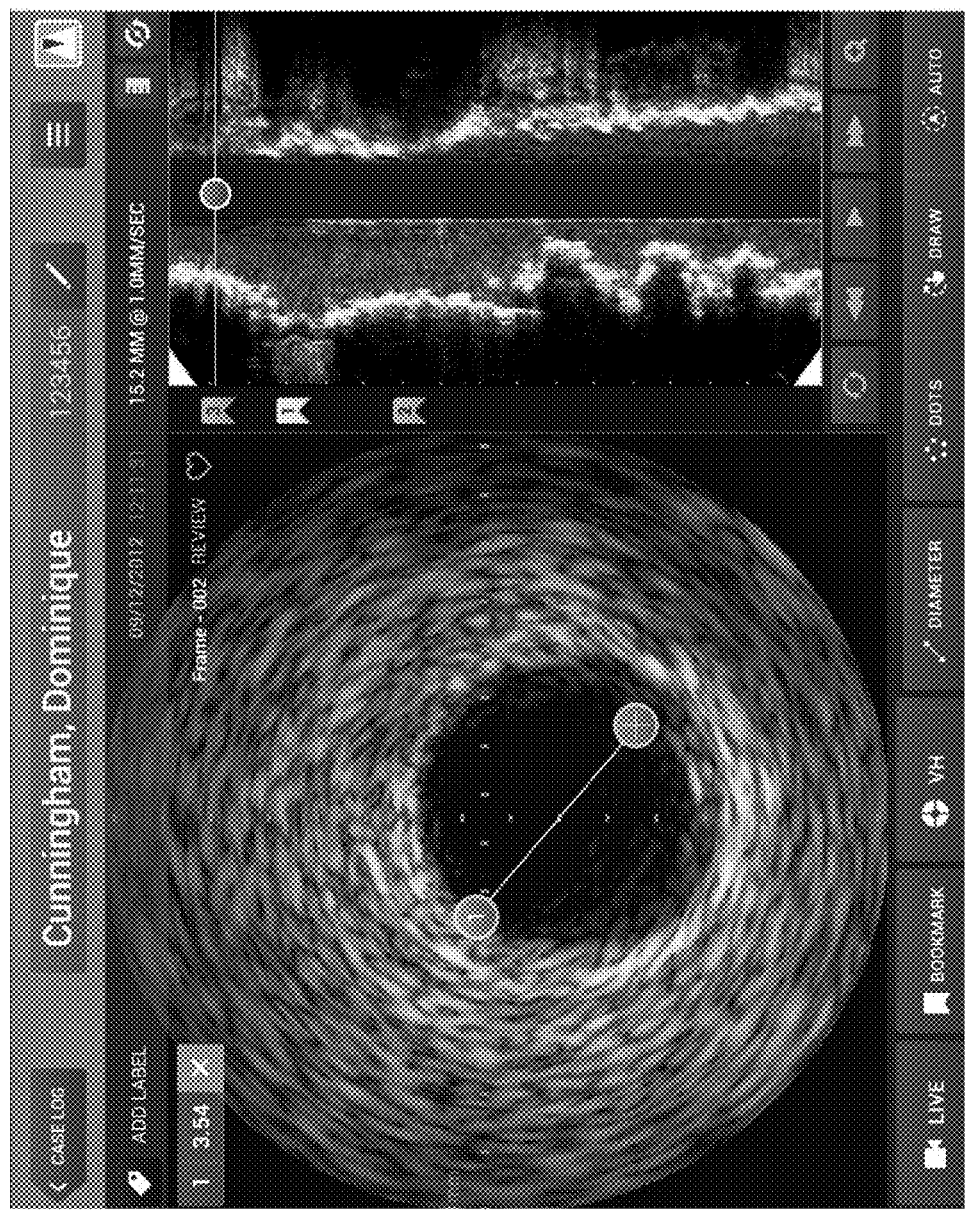
FIG. 7 illustrates an example acquired data review screen of a user interface rendered by the multi-modality processing system of FIG. 1.
Figure 8:
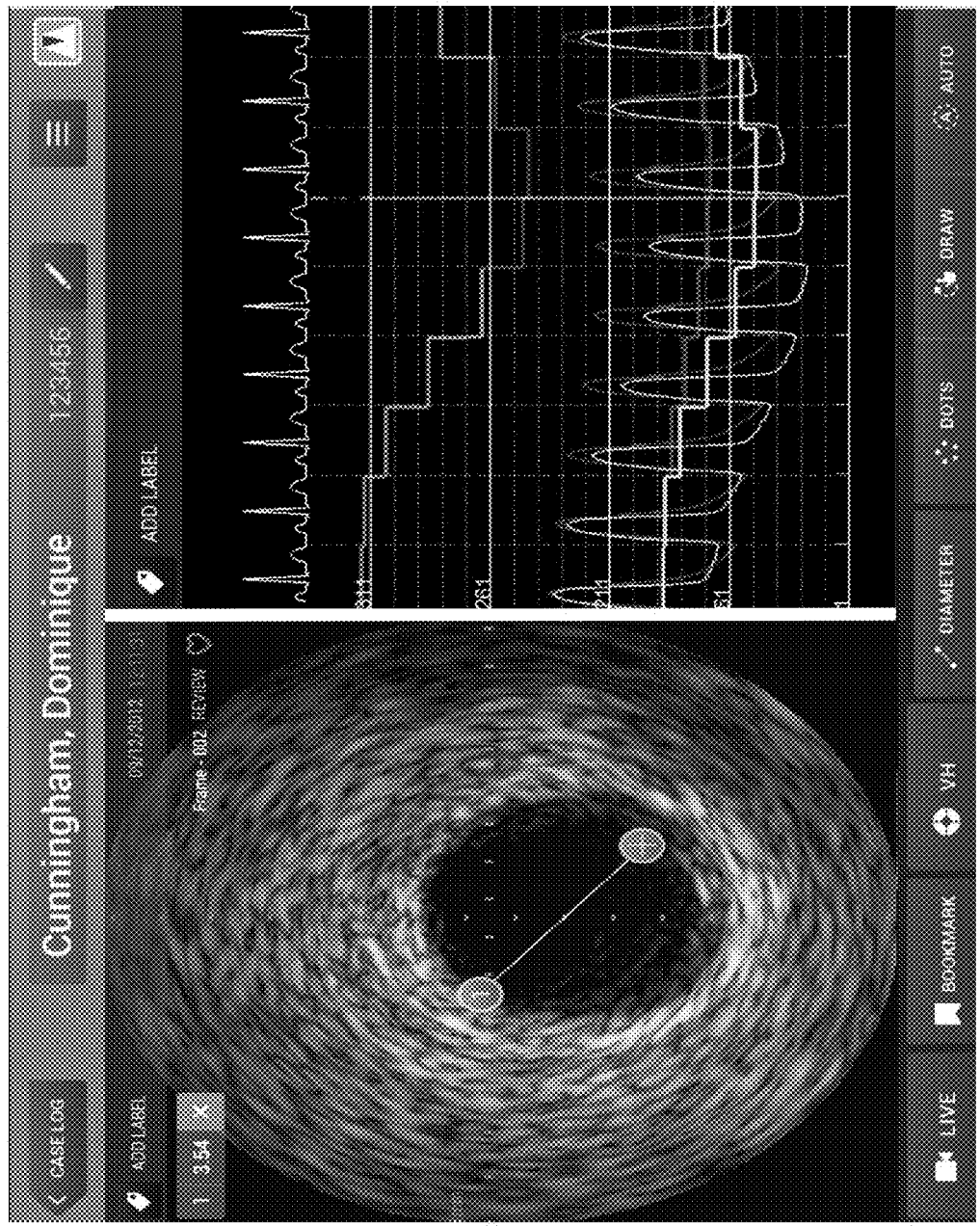
FIG. 8 is another example acquired data review screen but showing data associated with different modalities displayed side by side.

The data review states 512 and 516 of the GUI logic state machine 306 utilize activities 522 and 524 that implement tasks associated with the retrieval and review of previously-acquired IVUS data. The activities 522 and 524 include rendering an acquired data review screen including user interaction elements and displaying previously captured IVUS images. In one embodiment, upon receiving a user request in the user interface to display a specific IVUS data set, the GUI logic state machine 306 may transmit a request to the business logic state machine 304 to retrieve the request data set from the data repository. An example acquired medical data review screen is illustrated in FIG. 7. The example display screen shows an image data set captured during an IVUS acquisition procedure. In reviewing the IVUS images, a practitioner may make measurements and add labels and other annotations on the IVUS images in the data set. FIG. 8 is another example acquired medical data review screen but showing data associated with different modalities displayed side by side. Specifically, an IVUS image acquired from a patient is shown concurrently with FFR data collected from the same patient. The IVUS data and the FFR data may have been collected during the same catheter lab procedure or during different catheter lab procedures. The data review states 512 and 516 of the GUI logic state machine 306 may include synchronization activities to spatially or temporally synchronizing the multi-modality data displayed in the review screen. Methods and systems for management and display of previously acquired data in a multi-modality medical system are disclosed in U.S. Provisional Patent Application No. 61/746,897, entitled "MULTI-MODALITY CASE EXPLORER SYSTEM AND METHOD," which is hereby incorporated by reference in its entirety.

With reference back to FIG. 5, the review still display state 512 further utilizes activity modules to enable a user to make measurements of elements in an IVUS image and add annotations, drawings, and labels to an IVUS image. Also, the review still display state 512 includes an activity to enable a user to zoom into portions of an IVUS image. One of ordinary skill in the art would understand that the list of activities 522 and 522 associated with the data review states 512 and 516 are simply examples and the states 512 and 516 may include additional and/or different activities.

It is understood that the system and method described above for managing multi-modality workflows with state machines in a multi-modality processing system are simply example embodiments, and in alternative embodiments, additional and/or different steps may be included in the method and the system may include additional and/or different user interface screens.

Although illustrative embodiments have been shown and described, a wide range of modification, change, and substitution is contemplated in the foregoing disclosure and in some instances, some features of the present disclosure may be employed without a corresponding use of the other features. Further, as described above, the components and extensions described above in association with the multi-modality processing system may be implemented in hardware, software, or a combination of both. And the processing systems may be designed to work on any specific architecture. For example, the systems may be executed on a single computer, local area networks, client-server networks, wide area networks, internets, hand-held and other portable and wireless devices and networks. It is understood that such variations may be made in the foregoing without departing from the scope of the present disclosure. Accordingly, it is appropriate that the appended claims be construed broadly and in a manner consistent with the scope of the present disclosure.

What is claimed is:

1. A multi-modality medical system, comprising:
an intravascular ultrasound (IVUS) catheter sized and shaped for positioning within a vessel of a patient and including a transducer and configured to obtain IVUS data associated with an IVUS modality;
a medical instrument different than the IVUS catheter and configured to obtain medical data of a modality different than IVUS modality; and
a computing system communicatively coupled to the IVUS catheter and the medical instrument, the computing system including:
a plurality of activity modules configured to perform acquisition workflows, wherein the plurality of activity modules includes an energize activity module, a start pullback activity module, and a stop pullback activity module;
a first business logic state machine configured to control acquisition of the IVUS data from the patient with the IVUS catheter while the IVUS catheter is positioned within the vessel of the patient, wherein the first business logic state machine comprises an imaging ready state, the first business logic state machine entering the imaging ready state in response to coupling the IVUS catheter to the computing system, wherein the imaging ready state includes an IVUS imaging sub-state utilizing the plurality of activity modules, wherein, while the first business logic state machine is in the IVUS imaging sub-state:
in response to execution of the energize activity module, the computing system energizes the transducer of the IVUS catheter to obtain the IVUS data within the vessel,
in response to execution of the start pullback activity module, the computing system starts pullback of the IVUS catheter within the vessel, and
in response to execution of the stop pullback activity module, the computing system stops pullback of the IVUS catheter within the vessel; and
a second business logic state machine different than the first business logic state machine and configured to control acquisition of the medical data from the patient with the medical instrument, the second business logic state machine comprising one or more states utilizing the plurality of activity modules;
wherein the first and second business logic state machines each comprise a hierarchical sequence of actions executable using one or more of the plurality of activity modules to respectively control acquisition of the IVUS data and the medical data; and
wherein the plurality of activity modules is implemented in the computing system independently of the first and second business logic state machines such that each of the first and second business logic state machines can execute a same activity module during the respective hierarchical sequences of actions of the first and second business logic state machines to control the acquisition of the IVUS data with the IVUS catheter and to control the acquisition of the medical data with the medical instrument.

2. The multi-modality medical system of claim 1, wherein the computing system further includes an acquisition control activity module that is implemented independent of the first business logic state machine and the second business logic state machine.

3. The multi-modality medical system of claim 2,
wherein the first business logic state machine is configured to utilize the acquisition control activity module to control acquisition of the IVUS data from the patient with the IVUS catheter; and
wherein the second business logic state machine is configured to utilize the acquisition control activity module to control acquisition of the medical data from the patient with the medical instrument.

4. The multi-modality medical system of claim 2, wherein the acquisition control activity module is operable to perform at least one of energizing the transducer of the IVUS catheter, starting pullback of the IVUS catheter, and stopping pullback of the IVUS catheter.

5. The multi-modality medical system of claim 1, further comprising:
a first user interface state machine configured to receive the IVUS data from the first business logic state machine and present the IVUS data within a user interface, wherein the first user interface state machine comprises a live display state and a review full motion display state, wherein the first user interface state machine is operable to transition into the live display state during acquisition of the IVUS data and is operable to transition into the review full motion display state after acquisition of the IVUS data; and
a second user interface state machine configured to receive the medical data from the second business logic state machine and present the medical data within the user interface, wherein the second user interface state machine comprises a live display state and a review full motion display state, wherein the second user interface state machine is operable to transition into the live display state during the acquisition of the medical data and is operable to transition into the review full motion display state after acquisition of the medical data,
wherein the imaging ready state includes an initial sub-state defining a transition of the first business logic state machine to the IVUS imaging sub-state or another sub-state of the imaging ready state when the first business logic state machine enters the imaging ready state.

6. The multi-modality medical system of claim 5, wherein the computing system further includes an interface rendering activity module.

7. The multi-modality medical system of claim 6,
wherein the first user interface state machine is configured to utilize the interface rendering activity module to present the IVUS data within the user interface; and
wherein the second user interface state machine is configured to utilize the interface rendering activity module to present the medical data within the user interface.

8. The multi-modality medical system of claim 6, wherein the interface rendering activity module is operable to perform at least one of rendering an acquisition screen and rendering a review screen.

9. The multi-modality medical system of claim 6, wherein the interface rendering activity module is operable to perform at least one of adding a measurement to an image, adding an annotation to an image, and adding a label to an image.

10. The multi-modality medical system of claim 1, wherein the modality of the medical data includes one of intravascular photoacoustic (IVPA) imaging, optical coherence tomography (OCT), fractional flow reserve (FFR), angiography, or coronary flow reserve (CFR).

11. The multi-modality medical system of claim 5, wherein the first business logic state machine includes a data acquisition state and a data review state.

12. The multi-modality medical system of claim 11, wherein the first business logic state machine is operable to transition between the data acquisition state and the data review state based on user actuations of elements within the user interface.

13. The multi-modality medical system of claim 5,
wherein the first user interface state machine further includes an imaging idle display state, a freeze display state, a review still display state, and a recording display state, and
wherein the second user interface state machine further includes an imaging idle display state, a freeze display state, a review still display state, and a recording display state.

14. The multi-modality medical system of claim 13,
wherein the first user interface state machine is operable to transition among the imaging idle display state, the live display state the freeze display state, the review still display state, the review full motion display state, and the recording display state based on user actuations of elements within the user interface, and
wherein the second user interface state machine is operable to transition among the imaging idle display state, the live display state, the freeze display state, the review still display state, the review full motion display state, and the recording display state based on user actuations of elements within the user interface.

15. The multi-modality medical system of claim 5, wherein the hierarchical sequence of actions comprises a sub-state nested within a higher level state, and wherein the first and second business logic state machines and the first and second user interface state machines are configured respectively to control acquisition of the IVUS and medical data and to present the IVUS and medical data within the user interface by transitioning from the higher level state to the nested sub-state to execute the hierarchical sequence of actions.

16. The multi-modality medical system of claim 5, wherein the computing system further includes:
a resource arbiter component configured to coordinate utilization of common resources among a plurality of modality components to facilitate a multi-modality medical procedure;
a first modality component of the plurality of modality components, the first modality component in communication with the resource arbiter component and configured to control operations associated with the IVUS catheter, the first modality component comprising the first business logic state machine and the first user interface state machine; and
a second modality component of the plurality of modality components, the second modality component in communication with the resource arbiter component and configured to control operations associated with the medical instrument, the second modality component comprising the second business logic state machine and the second user interface state machine.

17. The multi-modality medical system of claim 1, wherein the computing system further comprises a data repository configured to store the IVUS data and medical data.

18. The multi-modality medical system of claim 1, wherein the first business logic state machine further comprises a waiting for imaging state, the first business logic state machine entering the waiting for imaging state in response to decoupling the IVUS catheter from the computing system.

19. A multi-modality medical workflow management method performed with a computing system communicatively coupled to an intravascular ultrasound (IVUS) catheter and a medical instrument different than the IVUS catheter, the method comprising:

positioning the IVUS catheter within a vessel of a patient, the IVUS catheter being sized and shaped for positioning within the vessel of the patient and including a transducer;

acquiring, with a first business logic state machine of the computing system, IVUS data from the patient with the IVUS catheter while the IVUS catheter is positioned within the vessel of the patient, the IVUS data associated with an IVUS modality, wherein the first business logic state machine comprises an imaging ready state, the first business logic state machine entering the imaging ready state in response to coupling the IVUS catheter to the computing system, wherein the imaging ready state includes an initial sub-state and an IVUS imaging sub-state utilizing a plurality of activity modules, wherein the plurality of activity modules is configured to perform acquisition workflows and includes an energize activity module, a start pullback activity module, and a stop pullback activity module, wherein, while the first business logic state machine is in the IVUS imaging sub-state:

in response to execution of the energize activity module, the computing system energizes the transducer of the IVUS catheter to obtain the IVUS data within the vessel, in response to execution of the start pullback activity module, the computing system starts pullback of the IVUS catheter within the vessel, and in response to execution of the stop pullback activity module, the computing system stops pullback of the IVUS catheter within the vessel;

acquiring, with a second business logic state machine different than the first business logic state machine, medical data of a modality different than the IVUS modality from the patient with the medical instrument, the second business logic state machine comprising one or more states utilizing the plurality of activity modules;

wherein the acquiring the IVUS data and the medical data includes executing a hierarchical sequence of actions using one or more of the plurality of activity modules, and wherein the plurality of activity modules is implemented in the computing system independently of the first and second business logic state machines such that each of the first and second business logic state machines can execute a same activity module during the respective hierarchical sequences of actions of the first and second business logic state machines to control the acquisition of the IVUS data with the IVUS catheter and to control the acquisition of the medical data with the medical instrument.

20. The multi-modality medical workflow management method of claim 19, wherein acquiring the IVUS data includes the first business logic state machine utilizing an acquisition control activity module to control acquisition of the IVUS data from the patient with the IVUS catheter; and wherein acquiring the medical data includes the second business logic state machine utilizing the acquisition control activity module to control acquisition of the medical data from the patient with the medical instrument.

21. The multi-modality medical workflow management method of claim 20, wherein utilizing the acquisition control activity module includes utilizing the acquisition control activity module to perform at least one of energizing the transducer of the IVUS catheter, starting pullback of the IVUS catheter, and stopping pullback of the IVUS catheter.

22. The multi-modality medical workflow management method of claim 19, further comprising:

presenting, with a first user interface state machine, the IVUS data within a user interface, wherein the first user interface state machine comprises a live display state and a review full motion display state, wherein the first user interface state machine is operable to transition into the live display state during acquisition of the IVUS data and is operable to transition into the review full motion display state after acquisition of the IVUS data; and presenting, with a second user interface state machine different than the first user interface state machine, the medical data within the user interface, wherein the second user interface state machine comprises a live display state and a review full motion display state, wherein the second user interface state machine is operable to transition into the live display state during the acquisition of the medical data and is operable to transition into the review full motion display state after acquisition of the medical data, wherein the initial sub-state defines a transition of the first business logic state machine to the IVUS imaging sub-state or another sub-state of the imaging ready state when the first business logic state machine enters the imaging ready state.

23. The multi-modality medical workflow management method of claim 22, wherein presenting the IVUS data includes the first user interface state machine utilizing an interface rendering activity module to present the IVUS data within the user interface; and wherein presenting the medical data includes the second user interface state machine utilizing the interface rendering activity module to present the medical data within the user interface.

24. The multi-modality medical workflow management method of claim 23, wherein utilizing the interface rendering activity module includes utilizing the interface rendering activity module to perform at least one of rendering an acquisition screen and rendering a review screen.

25. The multi-modality medical workflow management method of claim 23, wherein utilizing the interface rendering activity module includes utilizing the interface rendering activity module to perform at least one of adding a measurement to an image, adding an annotation to an image, and adding a label to an image.

26. The multi-modality medical workflow management method of claim 19, wherein the modality of the medical data includes one of intravascular photoacoustic (IVPA) imaging, optical coherence tomography (OCT), fractional flow reserve (FFR), angiography, or coronary flow reserve (CFR).

27. The multi-modality medical workflow management method of claim 22,
- wherein the first user interface state machine further includes an imaging idle display state, a freeze display state, a review still display state, and a recording display state,
- wherein the second user interface state machine further includes an imaging idle display state, a freeze display state, a review still display state, and a recording display state.

28. The multi-modality medical workflow management method of claim 27, wherein presenting the IVUS data includes transitioning among the imaging idle display state, the live display state, the freeze display state, the review still display state, the review full motion display state, and the recording display state based on user actuation of elements within the user interface.

\* \* \* \* \*